United States Patent [19]

Yetter, Jr.

[11] Patent Number: 4,541,425

[45] Date of Patent: Sep. 17, 1985

[54] HEAD AND TORSO RESTRAINT

[76] Inventor: Arthur M. Yetter, Jr., 100 Maple Shade Ave., Trenton, N.J. 08610

[21] Appl. No.: 572,194

[22] Filed: Jan. 19, 1984

[51] Int. Cl.$^4$ ............................................. A61F 13/00
[52] U.S. Cl. ..................................... 128/134; 297/464
[58] Field of Search ...................... 128/133, 134, 89 A; 297/464, 465, 467, 468, 469

[56] References Cited

U.S. PATENT DOCUMENTS

| | | | |
|---|---|---|---|
| 3,136,311 | 6/1964 | Lewis | 128/134 |
| 3,218,103 | 11/1965 | Boyce | 297/464 |
| 4,181,358 | 1/1980 | Pennington | 297/467 |
| 4,299,211 | 11/1981 | Doynow | 128/134 X |

Primary Examiner—John D. Yasko
Attorney, Agent, or Firm—William Lawrence Muckelroy; William Larence Muckelroy

[57] ABSTRACT

An accessory for an arm chair for use by a patient seated therein wherein a headband secured about the patient's head is attached to a strap at the back which is tied at the back of the chair to limit the degree of forward movement of the patient's head and wherein a pillow is placed adjacent each side of the patient in between each thigh of the patient and each side of the chair and wherein each pillow has attached thereto a strap which extends over a proximate shoulder of the patient and tied to the back of the chair for the purpose of restraining lateral movement of the patient's torso.

8 Claims, 4 Drawing Figures

HEAD AND TORSO RESTRAINT

BACKGROUND OF THE INVENTION

1. Field of the Invention:

The invention is related to a chair accessory for restraining lateral flexion of the torso and for limiting forward flexion of the head of a patient seated in a chair.

2. Description of the Prior Art:

The prior art includes various bib structures, none of which is known to have been generally accepted, the patents known being U.S. Pat. No. 4,170,991 which is a seat bib partly sat upon and in part similar to an ordinary bib; U.S. Pat. No. 2,170,703 which is represented as being for tying an infant in a highchair, this being accomplished by a bib with arm holes and an aperture through which the legs of the child are extended in addition to a crotch strap; U.S. Pat. No. 2,851,033 which shows a bib covering the front of a patient and provided with straps fastened around the back of the wheelchair and "underneath the (seat) chair", this arrangement not positively preventing the patient from accidentally or deliberately having his head slumped forward or from having the torso tilt or flexed to either side;

U.S. Pat. No. 4,182,322 issued to Larry C. Miller on Jan. 8, 1980 is related to a head restraining and safety support device for use with a body splint/litter apparatus, the apparatus having a head rest section at one end thereof. U.S. Pat. No. 3,100,484 issued to J. E. Berl on Aug. 13, 1963 is a belt for restricting movement of the torso of a handicapped patient or a person suffering some impairment. It is padded, quilted, covered, and taped for comfortable wear and sanitation. It is adjustable to any required length and oriented about the patients waist and attached about the back of the wheelchair. U.S. Pat. No. 2,452,103 issued to J. A. Conradt, et al on Oct. 26, 1948 is a head rest for restraining lateral movement of the head. U.S. Pat. No. 2,582,571 issued to A. M. Thoma on Jan. 15, 1952 is also a head rest intended for attachment to the back of seats in buses and trains to support a passenger's head and reduce annoying noises. U.S. Pat. No. 4,339,151 issued to Eric D. Riggs on July 13, 1982 is a head restraint for supporting the user's head. U.S. Pat. No. 2,619,362 discloses a restraining cushioning device for tethering children or restricting their movement in a motor vehicle. U.S. Pat. No. 4,097,086 discloses a body restraint for supporting persons while sleeping upright in a chair. The device disclosed in U.S. Pat. No. 4,097,086 employs a strap encircling the back of the chair and the torso of the user. The device also discloses a pillow attachable at one end to the strap against which the user may rest his "head".

The invention is also generally related to U.S. Pat. No. 3,136,311 issued to Sidney Lewis on June 9, 1964 which is a patient supporting garment, vest-like in nature and adapted for holding an invalid patient in a conventional sitting position on a chair or the like. Other harness type torso supports for invalids and bed-ridden patients are disclosed in U.S. Pat. No. 2,851,033 and 2,413,395.

Patients in chairs, for example wheelchairs, frequently require means to support and/or restrain them against inadvertent falling or sliding out of the chair as well as means for restraining lateral movement of their torso and forward flexion of the head at its juncture with the cervical spine to avoid injury to the cervical spine and/or injury to the lumbar spine or bruising of the rib cage when they fall asleep and after falling asleep either lean too far forward or lean too far laterally to either the right or the left from the upright seated position. A positive comfortable restraint for both the head and the torso is desirable. The commonest current method for preventing movement of the torso is an uncomfortable belt like restraint about the waist and sometimes also a bib around the chest or waist. The prior art appears devoid of any means for restraining forward flexion of the head. However, several designs for completely and uncomfortably restraining head motion of patients are disclosed in the prior art. Generally, these means are uncomfortable and not designed for use by sedentary, senile or handicapped patients who spend a substantial portion of their waking hours in a chair.

The prior art has been primarily directed towards restraining the torso of the wheelchair patient without any attention to the problem of cervical sprain which can be caused by traumatic, sudden flexion of the cervical spine by the head dropping as the patient falls asleep while being held in the chair. Moreover, the belt restraints and other restraints which are affixed around the torso of the patient have the disadvantage of having to be disconnected to allow the patient to be removed from the wheelchair or to remove himself from the wheelchair to attend to elimination.

An object of the present invention is to provide in combination with an armchair, a means for passively restraining lateral movement of the torso of the patient seated therein in a comfortable and effective manner without the necessity of having to tie an item about the body or the torso of the patient while simultaneously providing freedom of movement of the head backwards in an unlimited capacity and also lateral rotation in an unlimited capacity for eating and conversational purposes and at the same time providing restraint from severe forward flexion in the event that the patient falls asleep while seated in the chair.

A further object of the present invention is to provide a simple and inexpensive means for limiting forward flexion of the user's head and at the same time provide a relatively inexpensive means for limiting lateral flexion of the user's torso utilizing strips of fabric and pillows and pillowcases already in existence.

The need for this unique combination of a means for limiting forward flexion of the user's head and a means for limiting the lateral flexion of the user's torso has not been heretofore recognized in the art. However, the need for such a combination of restraints has existed for a considerable time but until now no inexpensive and disposable means was available.

SUMMARY OF THE INVENTION

As claimed, the present invention, representing a response to the above mentioned need, comprises a headband which is made of cloth and has attached thereto a cloth strap which is tied to the back of a chair with an appropriate amount of slack to permit usual movement of the user's head and only restrains substantial forward flexion of the head and further comprises two large pillows each covered by a pillowcase, one each being placed laterally to the patient in between the patient and an arm of an armed chair, each pillow rising up to the shoulder of the patient and each pillowcase having an aperture near the shoulder of the patient which is closed by a cloth strap attached to the pillowcase and whereby each cloth strap is of sufficient length to extend to the rear of the chair and tautly attached thereto by tying or other equivalant means.

DETAILED DESCRIPTION OF A PREFERRED EMBODIMENT OF THE INVENTION

Although as stated above, the accessories of the invention are adaptable for use with a wheelchair and are particularly described as manufactured of a cloth fabric, it is to be understood that the invention is not limited to such articles and that the accessories comprising the invention may be used with any chair having arm supports and having a comparable means at the back thereof for securing or tying of the cloth straps which extend from the headband and which are attached to the two pillows encased in the pillowcases described. Further, it is to be understood that the invention is the combination of the two pillows with straps and the headband with straps as used and connected to a chair or similar seating or standing apparatus.

Figure 1:
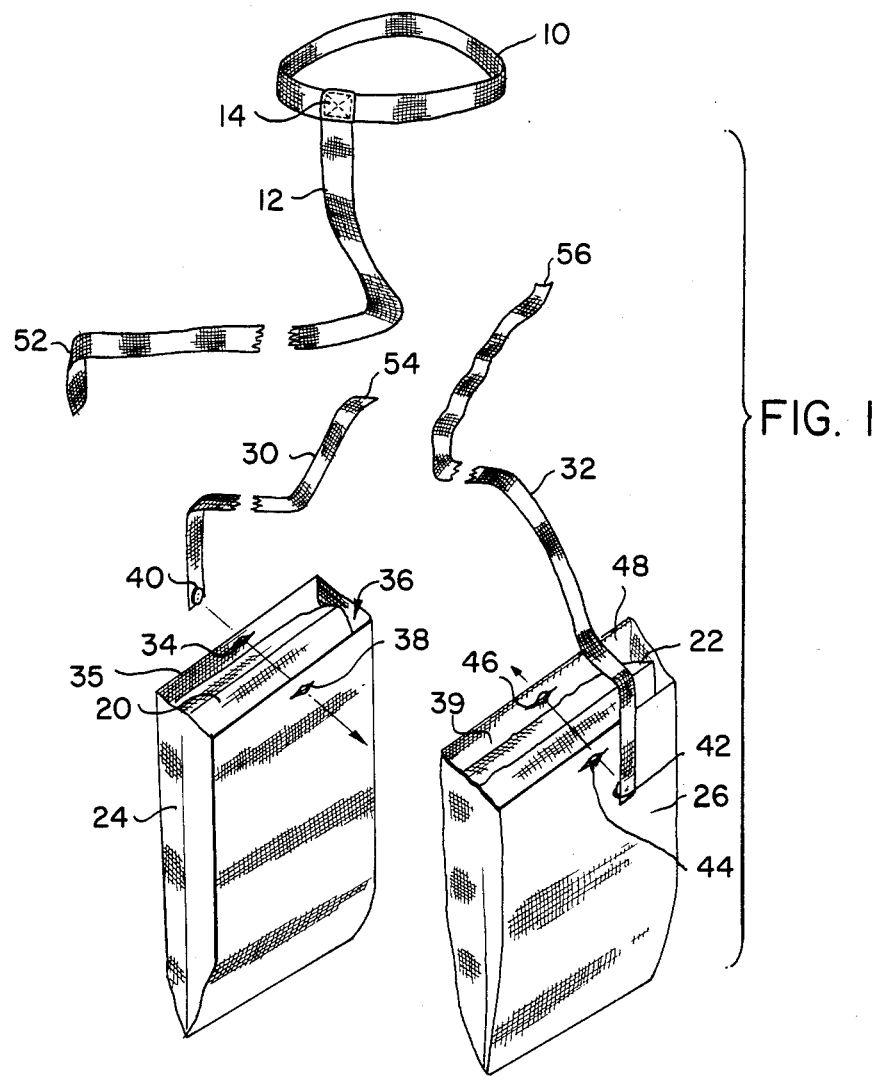
FIG. 1 is a perspective view of the new and novel means for restraining lateral movement of a user's torso in combination with means for limiting forward flexion of a user's head.

Referring in detail to the drawings, attention is directed to FIG. 1 wherein there is shown a preferred embodiment of the new and novel invention illustrating its essential features. Shown in FIG. 1 is a headband 10. The headband 10 has attached thereto a strap 12. Also shown in FIG. 1 is a means for attaching the strap 12 to the headband 10. The means shown in FIG. 1 for attachment is a combination of stitches 14 whereby the strap 12 is sewn to the headband 10.

Again referring to FIG. 1 there is shown a pair of pillows 20 and 22 covered by pillowcases 24 and 26, respectively. Further shown is an exploded view associated with the pillowcase 24 and a strap 30. Shown also is an exploded view associated with the pillowcase 26 and a strap 32. There is also shown a means for attaching each of the straps 30 and 32 to respective pillowcases 24 and 26. For attaching the strap 30 to the pillowcase 24 said means comprises a buttonhole 34 located near a periphery 35 of an aperture 36 of the pillowcase 24, for example. In allignment with buttonhole 34 is a buttonhole 38, which is medially also located with respect to the pillow 20 near a periphery 35 of the aperture 36 of the pillowcase 24. A button 40 is attached to the strap 30, by being sewn thereto, for example. The button 40 and the buttonholes 34 and 38 are sized such that the strap 30 may be securely fastened to the pillowcase 24 and close the aperture 36.

Similarly, the strap 32 has a similar means for attachment to the pillowcase 26. Said means comprises a button 42 which is attached to the pillowcase 26 via buttonholes 44 and 46. The buttonholes 44 and 46 are alligned and located near the edge 39 of an aperture 48 of the pillowcase 26. Buttonholes 44 and 46 are also medially located with respect to the pillow 22 near the edge 39 of the aperture 48. The button 42 is attached to the strap 32 by being sewn thereto. The button 42 is passed through the buttonholes 44 and 46 and closes the aperture 48. The buttonholes 44 and 46 are adapted to securely receive and hold the strap 32 to the pillowcase 26.

Each of the straps 12, 30 and 32 have free ends 52, 54 and 56, respectively for attachment to a chair (not shown in FIG. 1).

Figure 2:
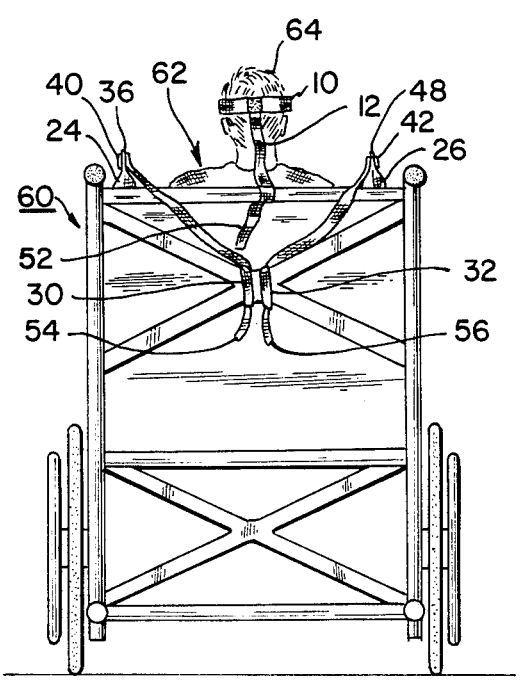
FIG. 2 is a rear view of the new and novel invention is use on a patient and in combination with a wheelchair.

Referring now to FIG. 2 of the drawings, there is shown a rear view of an arm chair, for example, a wheelchair 60. The wheelchair 60 has seated therein, a user having, for example, a torso 62. The head 64 on the torso 62 is shown with the headband 10 thereon. The strap 12 is tied to the wheelchair 60 with the end 52 of the strap 12 hanging therefrom. The strap 30 is tied to the back of the wheelchair 60, the strap 32 is also tied to the back of the wheelchair 60. The end 54 of the strap 30 hangs freely. The end 56 of the strap 32 also hangs freely behind the wheelchair 60. Although the straps 30 and 32 are tied to the back of the wheelchair 60, they may be secured by any number of means. Attachment of the straps 30 and 32 by tying is merely to exemplify the best mode.

Shown from the rear of the chair 60 are pillowcases 24 and 26 with their respective apertures 36 and 48 closed by a means for attaching thereto the straps 30 and 32, respectively. The means for attaching the strap 30 to the pillowcase 24 is, for example, button 40 as sewn to the strap 30. The means for attaching the strap 32 to the pillowcase 26, is for example, button 42 as sewn to the strap 32.

As shown, the button 40 secures the aperture 36 of the pillowcase 24 closed. The button 42 secures the aperture 48 of the pillowcase 26 closed.

The straps 30 and 32 are drawn taut before being tied to the rear or back of the wheelchair or chair 60 so as to enhance and improve a means for limiting lateral flexion of the torso 62.

In FIG. 2 the pillowcase 24 (with the pillow 20 therein as shown in FIG. 1) is secured to the chair 60 by means of a strap 30. The pillowcase 24 works in combination with the pillowcase 26 (with the pillow 22 therein as shown in FIG. 1) when secured to the chair 60 by means of the strap 32 to limit lateral movement of the torso 62. Further, the headband 10, when attached to the chair 60 by means of the strap 12, acts in combination with the chair 60 to restrain forward flexion of the head 64 attached to the torso 62.

Figure 3:
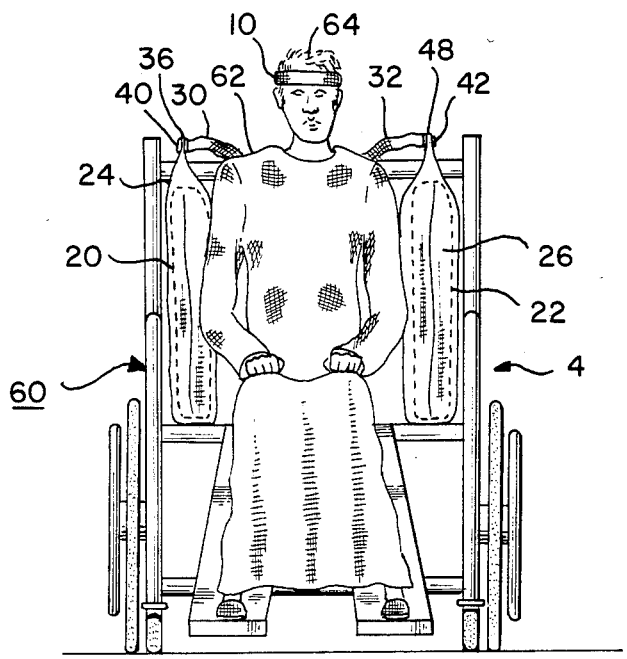
FIG. 3 is a front view of the new and novel invention in combination with a wheelchair in use on a patient.

FIG. 3 is a frontal view of the combination of the invention in use. Shown there is the pillowcase 26 with the pillow 22 inside. As shown, the pillowcase 26 has its aperture 48 closed by the button 42 which is attached to the strap 32. Similarly, as shown, the pillowcase 24 with the pillow 20 therein has its aperture 36 closed by the button 40 which is attached to the strap 30. The pillowcase 24 with the pillow 20 therein is located adjacent one lateral aspect (left side) of the torso 62 in between the torso 62 and the chair 60. The pillowcase 26 with the pillow 22 therein is located adjacent another lateral aspect (right side) of the torso 62 in between the torso 62 and the chair 60. The pillows 20 and 22 are oriented such that each extends along an entire side of the torso 62 to a point where each is approximately at shoulder height with the torso 62. Lateral movement of the torso 62 is restrained by orientation and positioning of the pillows 20 and 22 as shown and the securing of the pillows 20 and 22 in place by means of the straps 30 and 32, respectively which are attached to the pillowcases 24 and 26, respectively.

Figure 4:
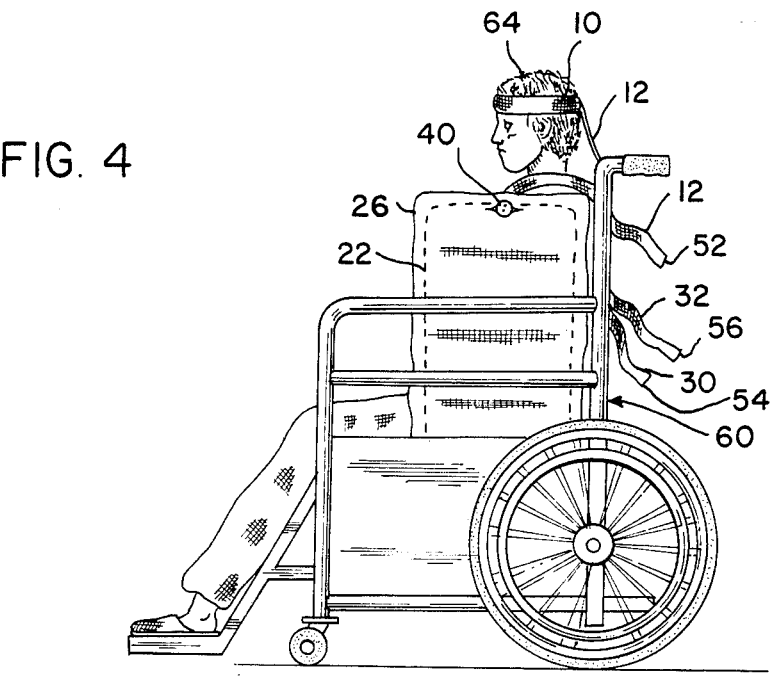
FIG. 4 is a side view of the new and novel invention in combination with a wheelchair.

FIG. 4 is a left lateral view of FIG. 3 from the left side of the head 64 taken in the direction 4 shown in FIG. 3. Shown there is the chair 60, the pillow case 26 (with the pillow 22 therein) adjacent the torso 62. The pillow 22 is located in between the torso 62 at the left lateral side thereof and in between the torso 62 and the left side of the chair 60. The button 40 is shown along with the end 56 of the strap 32. Similarly, there is shown the strap 30 and the end thereof 54. The headband 10 is shown affixed about the head 64. The strap 12 is tied to the chair 60 with the end 52 thereof shown dangling free beyond the wheelchair 60.

Finally, although not shown, the straps 12, 30 and 32 may be attached to the wheelchair by panels of an inter-engaging fastening means of suitable character, said panels may be affixed to selected aspects of the chair 60 and at selected positions along one side of the straps 12, 30 and 32. These pads may be made of inter-engaging elements sold under the trademark VELCRO. Similarly, the size of the headband 10 may be adapted to be adjustable by forming the headband 10 from a strip joined together at the end thereof by use of lengths of said VELCRO at the two adjoining ends of the strip.

I claim:

1. In combination with a chair having arm supports, a human head and torso restraint for supporting a user's head and torso while seated in said chair comprising means for limiting forward flexion movement being attached to said chair, means for limiting lateral flexion of the user's torso, said means for limiting lateral flexion of the user's torso being attached to said chair, said means for limiting lateral flexion of the user's torso further comprising a left means for limiting left lateral flexion in combination with a right means for limiting right lateral flexion, wherein said left and right means each comprises a pillow covered by a pillow case placed adjacent a side of the user in between the user and an arm support and having a means for interconnecting each said pillow case and said chair whereby lateral flexion of a user's torso is restrained by said pillow.

2. The combination of claim 1 wherein said means for limiting forward flexion of a user's head comprises a headband having a front and a back and means for connecting said headband to said chair attached to the back of said headband.

3. The combination of claim 2 wherein said means for interconnecting each said pillowcase to said chair comprises a left strap connected to said left means and a right strap connected to said right means, said left and right straps being detachably tied to said chair and wherein said means for connecting said headband to said chair comprises a third strap which is detachably tied to a rear part of said chair.

4. The combination of claim 3 wherein said pillow is sufficiently firm to provide resistance to lateral movement by said user and wherein said pillowcase has an aperture which is adapted at the periphery thereof with means for detachably receiving and connecting to straps.

5. The combination of claim 4 wherein each pillow has a broad side and each pillow is oriented with a broad side adjacent a shoulder of said user.

6. The combination of claim 5 wherein said left and right straps each has a means for detachably fastening one end thereof to one of said pillowcases.

7. The combination of claim 6 wherein said means for detachably fastening one end of each of said left and right straps to a pillowcase comprises a button attached to each strap and wherein said means for detachably receiving and connecting to a strap comprises buttonholes in allignment on each side of said pillowcase near the periphery of said aperture, said buttonholes being adapted to receive said button.

8. The combination of claim 2 wherein said means for limiting lateral flexion and said means for limiting forward flexion are comprised of washable cloth whereby an increased measure of comfort is achieved for the user.

* * * * *